US008192590B1

(12) United States Patent
Belfield et al.

(10) Patent No.: US 8,192,590 B1
(45) Date of Patent: Jun. 5, 2012

(54) MICROWAVE-ASSISTED FORMATION OF SULFONIUM PHOTOACID GENERATORS

(75) Inventors: Kevin D. Belfield, Oviedo, FL (US); Ciceron O. Yanez, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 290 days.

(21) Appl. No.: 12/422,724

(22) Filed: Apr. 13, 2009

Related U.S. Application Data

(60) Provisional application No. 61/044,722, filed on Apr. 14, 2008.

(51) Int. Cl.
*C07B 45/00* (2006.01)
*A01N 35/06* (2006.01)
*B01J 19/12* (2006.01)
*C07F 9/02* (2006.01)

(52) U.S. Cl. ......... 204/157.76; 204/157.77; 204/157.78; 204/157.73; 204/157.7

(58) Field of Classification Search ............. 204/157.73, 204/157.76, 157.77, 157.78, 157.7
See application file for complete search history.

(56) References Cited

U.S. PATENT DOCUMENTS

| | | | | | |
|---|---|---|---|---|---|
| 2,807,648 | A | * | 9/1957 | Pitt | 568/74 |
| 4,250,311 | A | * | 2/1981 | Crivello | 546/9 |
| 5,084,586 | A | * | 1/1992 | Farooq | 556/181 |
| 5,124,417 | A | * | 6/1992 | Farooq | 526/90 |
| 5,830,417 | A | * | 11/1998 | Kingston | 422/186.29 |
| 5,883,349 | A | * | 3/1999 | Kingston | 204/157.43 |
| 6,620,957 | B1 | * | 9/2003 | Tomita et al. | 558/20 |
| 7,459,106 | B2 | * | 12/2008 | Marder et al. | 252/600 |
| 7,611,817 | B2 | * | 11/2009 | Nakayashiki et al. | 430/270.1 |

OTHER PUBLICATIONS

Goethals and de Radzitzky, "Reactions du Sulfoxyde de Dimethyle I—Synthese des halogenures de dimethyl-hydroxyaryl-sulfonium et pyrolyse de ces corps en methyl-hydroxyaryl thioethers," Bulletin des Societes Chimiques Belges, v. 73, Issue 5-6, pp. 546-559 (1964) (Abstract only).*
Kaehr, B., Shear, J., Mask-Directed Multiphoton Lithography, Journal of the American Chemical Society, 2007, pp. 1904-1905, vol. 129, No. 7.
Belfield, K., Schafer, K., Liu, Y., Liu, J., Ren, X., Stryland, E., Multiphoton-Absorbing Organic Materials for Microfabrication, Emerging Optical Applications and Non-Destructive Three-Dimensional Imaging, Journal of Physical Organic Chemistry, 2000, pp. 837-849, vol. 13.

(Continued)

*Primary Examiner* — Keith Hendricks
*Assistant Examiner* — Colleen M Raphael
(74) *Attorney, Agent, or Firm* — Brian S. Steinberger; Joyce Morlin; Law Offices of Brian S. Steinberger, P.A.

(57) ABSTRACT

Efficient method for preparing sulfonium photoacid generators (PAGs) by microwave-assisted reaction of diarylsufides in the presence of alkylaryliodonium salts. Microwave-assisted synthesis of the PAGs is significantly faster, reducing reaction time with less energy consumption. Reaction times using the microwave-assisted synthesis are in a range of from 90 to 420 faster than conventional thermal conditions. The photoacid quantum yields of several salts prepared by the microwave reaction were measured; the photoacid quantum yields of new sulfonium PAGs were in a range from 0.01 to 0.4 times greater than yields from conventional synthesis. Incorporating a nitro group in the structures of the sulfonium salts increased photoacid quantum yield, induced intersystem crossing and increased the efficiency of photoacid generation compounds.

17 Claims, 6 Drawing Sheets

Δ = conventional heating
MW = microwave heating

OTHER PUBLICATIONS

Maruo, S., Nakamura, O., Kawata, S., Three-Dimensional Microfabrication with Two-Photon-Absorbed Photopolymerization, Optic Letters, 1997, pp. 132-134, vol. 22, No. 2.

Schafer-Hales, K., Belfield, K, Yao, S., Fredericksen, P., Hales, J., Kolattukudy, P., Fluorene-Based Fluorescent Probes with High Two-Photon Action Cross-Sections for Biological Multiphoton Imaging Applications, Journal of Biomedical Optics, 2005, pp. 051402-1-051402-8, vol. 10, No. 5.

Denk, W., Strickler, J., Webb, W., Two-Photon Laser Scanning Fluorescence Microscopy, American Association for the Advancement of Science, 1990, pp. 73-76, vol. 248, No. 4951.

Corredor, C., Huang, Z., Belfield, K., Two-Photon 3D Optical Data Storage via Fluorescence Modulation of an Efficient Fluorene Dye by a Photochromic Diarylethene, Advanced Materials, 2006, pp. 2910-2914, vol. 18.

Parthenopoulos, D., Rentzepis, P., Three-Dimensional Optical Storage Memory, American Association for the Advancement of Science, 1989, pp. 843-845, vol. 245, No. 4920.

Beak, P., Sullivan, T., One-Electron Chemical Reductions of Phenylalkylsulfonium Salts, Journal of the American Chemical Society, 1982, pp. 4450-4457, vol. 104, No. 16.

Crivello, J., The Discovery and Development of Onium Salt Cationic Photoinitiators, Journal of Polymer Science: Part A: Polymer Chemistry, 1999, pp. 4241-4254, vol. 37.

Belfield, K., Schafer, K., Mourad, W., Reinhardt, B., Synthesis of New Two-Photon Absorbing Fluorene Derivatives via Cu-Mediated Ullmann Condensations, The Journal of Organic Chemistry, 2000, pp. 4475-4481, vol. 65, No. 15.

Varma, R., Saini, R., Microwave-Assisted Reduction of Carbonyl Compounds in Solid State Using Sodium Borohydride Supported on Alumina, Tetrahedron Letters, 1997, pp. 4337-4338, vol. 38, No. 25.

Belfield, K., Bondar, M., Przhonska, O., Schafer, K., One- and Two-Photon Photostability of 9,90didecyl-2, 7-bis(N,N-diphenylamino) Fluorene, The Royal Society of Chemistry, 2004, pp. 138-141, vol. 3.

Dektar, J., Hacker, N., Photochemistry of Diaryliodonium Salts, The Journal of Organic Chemistry, 1990, pp. 639-647, vol. 55, No. 2.

Jeon, S., Malyarchuk, V., Rogers, J., Fabricating Three Dimensional Nanostructures Using Two Photon Lithography in a Single Exposure Step, Optics Express, 2006, pp. 2300-2308, vol. 14, No. 6.

Belfield, K., Schafer, K, A New Photosensitive Polymeric Material for WORM Optical Data Storage Using Multichannel Two-Photon Fluorescence Readout, Chemistry of Materials, 2002, pp. 3656-3662, vol. 14, No. 9.

Dektar, J., Hacker, N., Photochemistry of Triarylsulfonium Salts, Journal of the American Chemical Society, 1990, pp. 6004-6015, vol. 112, No. 16.

Belfield, K., Ren, X., Stryland, E., Hagan, D., Dubikovsky, V., Miesak, E., Near-IR Two-Photon Photoinitiated Polymerization Using a Fluorene/Amine Initiating System, Journal of the American Chemical Society, 2000, pp. 1217-1218, vol. 122, No. 6.

Schafer, K., Hales, J., Balu, M., Belfield, K., Stryland, E., Hagan, D., Two-Photon Absorption Cross-Sections of Common Photoinitiators, Journal of Photochemistry and Photobiology A:Chemistry, 2004, pp. 497-502, vol. 162.

Lidstrom, P., Tierney, J., Wathey, B., Westman, J., Microwave Assisted ORganic Synthesis—A Review, Tetrahedron Journal, 2001, pp. 9225-9283, vol. 57.

Milsson, P., Olofsson, K., Larhed, M., Microwave-Assisted and Metal Catalyzed Coupling Reactions, Top Curr. Chem., 2006, pp. 103-144, vol. 266.

Seipel, K., Platt, Z., Nguyen, M., Holland, A., Microwave-Assisted Synthesis of Phenylene-Bridged Aminophosphine Ligands: Acceleration of N-Arylation and Aryl Fluoride Phosphorylation Reactions, The Journal of Organic Chemistry, 2008, pp. 4291-4294, vol. 73, No. 11.

Langa, F., Cruz, P., Hoz, A., Diaz-Ortiz, A., Diez-Barra, E., Microwave Irradiation: More Than Just a Method for Accelerating Reactions, Contemporary Organic Synthesis, 1997, pp. 373-386.

Crivello, J., Lam, J., A New Preparation of Triarylsulfonium and -Selenonium Salts via the Copper(II)-Catalyzed Arylation of Sulfides and Selenides with Diaryliodonium Salts, The Journal of Organic Chemistry, 1978, pp. 3055-3058, vol. 43, No. 15.

He, G., Bhawalkar, J., Zhao, C., Park, C., Prasad, P., Two-Photon-Pumped Cavity Lasing in a Dye-Solution-Filled Hollow-Fiber System, Optics Letters, 1995, pp. 2393-2395, vol. 20, No. 23.

Ehrlich, J., Wu., X., Lee, L., Hu, Z., Rockel, H., Marder, S., Perry, J., Two-Photon Absorption and Broadband Optical Limiting with Bis-Donor Stilbenes, Optics Letters, pp. 1843-1845, vol. 22, No. 24, Dec. 15, 1997.

Yanez, C., Andrade, C., Belfield, K., Characterization of Novel Sulfonium Photoacid Generators and Their Microwave-Assisted Synthesis , pp. S1-S13, Chem. Comm., Jan. 7, 2009, The Royal Society of Chemistry.

Sivasubramanian, S., Ravichandran, K., Synthesis of o/p-arylthiobenzaldehydes and o/p-methylsulphonylbenzaldehydes, Indian Journal of Chemistry, 1991, pp. 1148-1149, vol. 30B.

Belfield, K., Yao, S., Morales, A., Hales, J., Hagan, D., Stryland, E., Chapela, V., Percino, J., Synthesis and Characterization of Novel Rigid Two-Photon Absorbing Polymers, Polymers for Advanced Technologies, 2005, pp. 150-155, vol. 16.

Belfield, K., Schafer, K., Mourad, W., Reinhardt, B., Synthesis of New Two-Photon Absorbing Fluorene Derivatives via Cu-Mediated Ullmann Condensations, The Journal of Organic Chemistry. pp. 4475-4481, vol. 65, No. 15, Jul. 28, 2000 (published on web Jun. 27, 2000).

Pohlers, G., Scaiano, J., Sinta, R., Brainard, R., Pai, D., Mechanistic Studies of Photoacid Generation from Substituted 4,6-Bis(trichloromethyl)-1,3,5-triazines, Chemistry of Materials, 1997, pp. 1353-1361, vol. 9, No. 6.

Otsubo, T., Gray, R., Boekelheide, V., Bridged [18]annulenes. 12b, 12c, 12d, 12e, 12f, 12g-Hexahydrocoronene and its Mono- and Dibenzo Analogs. Ring-Current Contribution to Chemical Shifts as a Measure of Degree of Aromaticity, Journal of the American Chemical Society, 1978, pp. 2449-2456, vol. 100, No. 8.

Lakowicz, J., Instrumentation for Fluorescence Spetroscopy, Principles of Fluorescence Spectroscopy, 1999, pp. 25-61.

Yanez, C., Andrade, C., Belfield, K., Characterization of Novel Sulfonium Photoacid Generators and Their Microwave-Assisted Synthesis, The Royal Society of Chemistry, 2009, pp. 827-829.

* cited by examiner

Δ = conventional heating
MW = microwave heating

Δ = conventional heating
MW = microwave heating

Δ = conventional heating
MW = microwave heating

Δ = conventional heating
MW = microwave heating

MW = microwave heating

MICROWAVE-ASSISTED FORMATION OF SULFONIUM PHOTOACID GENERATORS

This application claims the benefit of priority from U.S. Provisional Patent Application Ser. No. 61/044,722 filed Apr. 14, 2008 and is incorporated herein by reference;

The research was supported in part by the National Science Foundation under Grants # ECS-0621715 and ECS-0524533.

FIELD OF THE INVENTION

This invention relates to photoacid generators and, in particular, to methods, systems, apparatus and devices for preparing sulfonium salt photoacid generators (PAGs) using microwave-assisted reactions.

BACKGROUND AND PRIOR ART

Since their discovery, the use of photoacid-generators, PAGs, has been widely adopted by the polymer industry in coatings, paints, anticorrosives, and electronics as described in Crivello, J. C. *Journal of Polymer Science Part A: Polymer Chemistry* (1999), 37, pp. 4241-4254.

The use PAGs in epoxide photoresists has been extensively studied for two-dimensional (2D) and three-dimensional (3D) lithographic patterning induced by one-photon absorption (1PA) and two-photon absorption (2PA) as described in Jeon, S.; Malyarchuk, V.; Rogers, J. A.; Wiederrecht, G. P. *Optics Express* (2006), 14, pp. 2300-2308 and Kim, E. K.; Ekerdt, J. G.; Willson, C. G. *Journal of Vacuum Science & Technology B* (2005), 23, pp. 1515-1520.

Two-photon absorption (2PA) has been reported for a number of applications, exploiting the fact that the 2PA probability is directly proportional to the square of the incident light intensity (dw/dt $\alpha I^2$) according to M. Goeppert-Mayer in *Ann. Phys.* (*Paris*) 1931, 9, 273; while one-photon absorption bears a linear relation to the incident light intensity, dw/dt $\alpha I$). This intrinsic property of 2PA leads to 3D spatial localization, important in fields such as optical data storage, fluorescence microscopy, and 3D micro-fabrication.

There have been demonstrations of successful two-photon microfabrication using commercial PAGs, as reported by Belfield, K. et al. in *J. Phys. Org. Chem.* 200, 13, 837-849 and Belfield, K. et al in *J. Am. Chem. Soc.,* 2000, 122, 1217-1218 even though the 2PA cross section of these initiators is low according to Schafer, K. et al. in *J. Photochem. Photobiol., A.* 2004, 162, 497-502. Two-photon 3D microfabrication with a novel PAG was reported to fabricate MEMs structures by Yu, T. et al. in *Advanced Materials.* 2003, 15, 517-521. To further advance a number of emerging technologies, there is a great need for photoacid generators (PAGs) with higher 2PA cross sections.

The synthesis of a class of photoacid generators such as, triarylsulfonium salts, by photolysis of the diphenyliodonium counterpart in the presence of a diphenylsulfide was originally reported by Crivello et al. in *Abstr. Pap. Am. Chem. Soc.,* 1978, 176, 8-8 and *J. Org. Chem.* 1978, 43, 3055-3058.

Microwave-facilitated synthesis has been the subject of substantial interest over the last decade, as reported by Lidstrom, P. et al. in *Tetrahedron.* 2001, 57, 9225-9283 and Niilsson, P. et al. in *Microwave Methods in Orsranic Synthesis* 2006, vol. 266, 103-104. Seipel at al in *J. Org. Chem.* 2008, 73, 4291-4294 recently reported microwave-assisted reaction times are 80 times faster than conventional heating reaction times, and are potentially more energy-efficient than conventional heating. There are no known reports of the microwave-assisted synthesis of sulfonium salts and no knowledge that microwave assisted synthesis would provide the advantage of reducing reaction times, which is extremely useful and cost efficient.

Incorporated herein by reference ar two publications by the inventors: Ciceron O. Yanez et al., "Chataterization of novel sulfonium photoacid generators and their microwave-assisted synthesis," in *Chemical Communications,* 2009, 827-829, Jan. 7, 2009 and Kevin D. Belfield et al., "New Photosensitive Polymeric Materials for Two-Photon 3D WORM Optical Data Storage" presented at American Chemical Society Meeting, Philadelphia, Pa., August 2008, both published after the priority date of the U.S. Provisional Application Ser. No. 61/044,722 filed Apr. 14, 2008 from which the present invention claims the benefit of priority.

The present invention discloses a facile, microwave-assisted synthesis of triarylsulfonium salt photoacid generators (PAGs) suitable for use as two-photon absorbing (2PA) photoinitiators, in negative resists for photolihtography or 3-D microfabrication, or in optical data storage.

SUMMARY OF THE INVENTION

A primary objective of the invention is to provide methods, apparatus and systems for an efficient method for preparing sulfonium photoacid generators (PAGs) by microwave-assisted reaction of diphenylsufides in the presence of diphenyliodonium salts.

A second objective of the invention is to provide methods, apparatus and systems for microwave-assisted synthesis of the PAGs that is significantly faster, in a range from 90 to 420 times faster than conventional thermal conditions, reducing reaction time with energy consumption.

A third objective of the invention is to provide methods, apparatus and systems for microwave-assisted synthesis of the PAGs with photoacid quantum yields of sulfonium PAGs ranging from 0.01 to 0.4.

A fourth objective of the invention is to provide novel photoacid generators (PAGs) for use as 2PA photoinitiators in negative resists for three-dimensional (3D) microfabrication.

A fifth objective of the invention is to provide novel photoacid generators (PAGs) for use as 2PA photoinitiators in optical data storage.

A preferred method for synthesizing sulfonium salts includes providing diaryl iodonium salts in the presence of diaryl sulfides, and exposing the diaryl iodonium salts in the presence of diaryl sulfides to microwave radiation for assisted formation of triaryl sulfonium salt photoacid generators.

The preferred diaryl iodonium salt is selected from at least one of a diphenyl iodonium salt. The preferred diaryl sulfide is selected from at least one of a diphenyl sulfide.

It is also preferred that the diaryl iodonium salt include a fluorene compound that forms the core structure of the triaryl sulfonium salt photoacid generator. The preferred fluorene compound is substituted with at least one of a stilbene motif, a thiophene motif and a nitro group at the 2- and 7-positions; more preferably, the fluorene compound is substituted with a nitro group at the 7-position.

In the preferred method, the reaction time for the synthesis of the sulfonium salt photoacid generator is in a range from approximately 30 seconds to approximately 10 minutes; more preferably, the reaction time for the formation of the sulfonium salt photoacid generator is approximately 6 minutes, which is in a range from approximately 90 to approximately 420 times faster than conventional thermal conditions.

Another preferred method for increasing the efficiency of photoacid generation by inducing intersystem crossing includes a process for synthesizing sulfonium salts including, selecting a glass reaction vessel suitable for use in a microwave reactor, mixing a fluorene compound that incorporates a nitro group with a diarylsulfide in the glass reaction vessel, purging the mixture with nitrogen gas while stirring, placing the nitrogen purged mixture in a microwave reactor. setting the microwave reactor containing the mixture of nitro-group fluorene compound and diarylsulfide to closed vessel, standard mode, maximum pressure 250 psi, maximum temperature 150 C, maximum power 60 watts and high speed stirring, running the reactor for thirty seconds and holding for 30 minutes, removing a nitro-containing, triarylsulfonium salt that exhibits increased photoacid quantum yield in a range of from approximately 0.01 to approximately 0.4 times greater than yields from conventional synthesis.

The preferred method for increasing the efficiency of photoacid generation uses a fluorene compound that incorporates a nitro group is 9,9-didecyl-2-iodo-7-nitro-9H-fluorene and a diarylsulfide that is vinyl sulfide.

Further objects and advantages of this invention will be apparent from the following detailed description of preferred embodiments which are illustrated schematically in the accompanying drawings.

DESCRIPTION OF THE PREFERRED EMBODIMENTS

Figure 1:
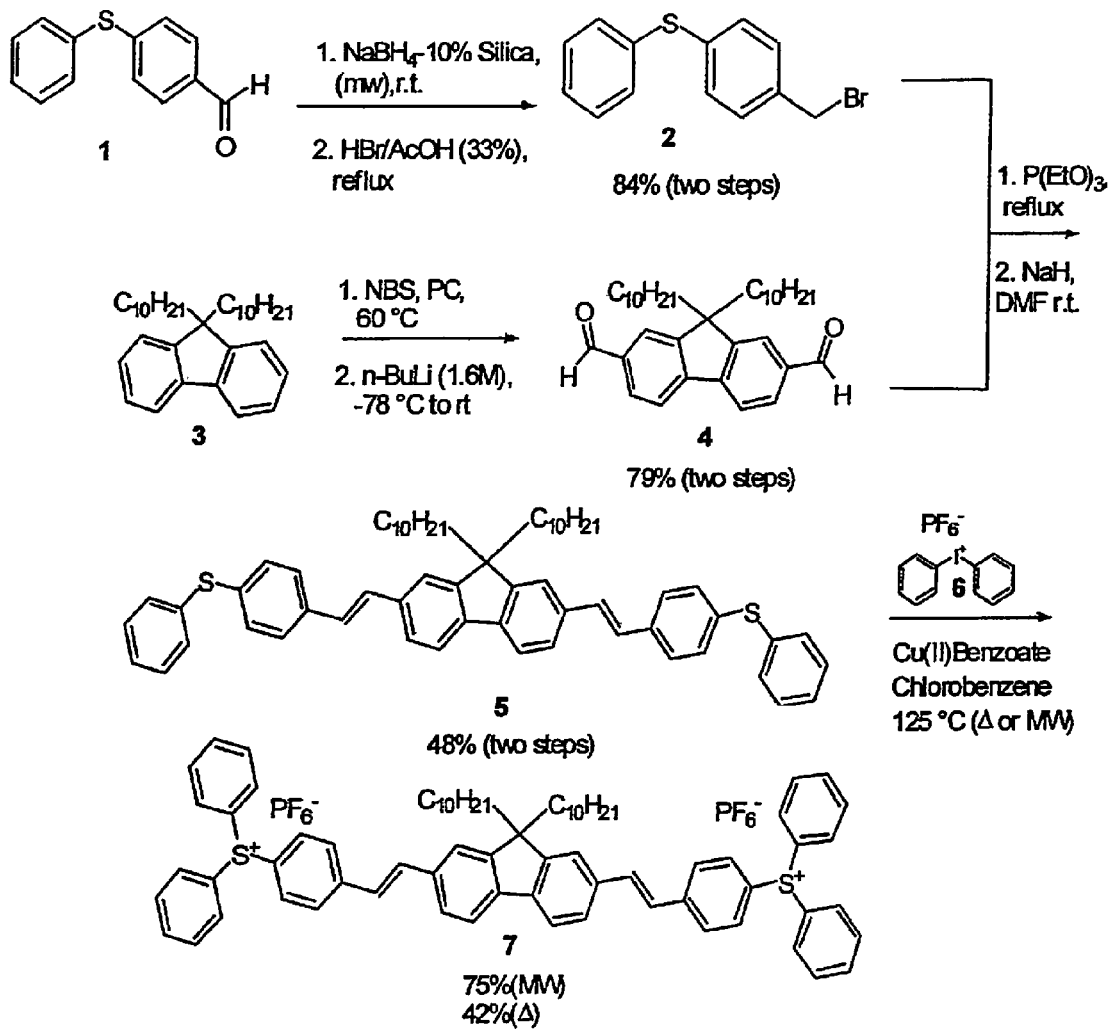
FIG. 1 shows a synthesis scheme for a photoacid generator PAG 7 wherein reactions are carried out both by conventional methods (Δ) and microwave heating (MW).

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

It would be useful to discuss the definitions of some words and abbreviations used herein and their application in explaining the invention.

"CEM Corporation" is the manufacturer microwave synthesis equipment, including the Discover™ System which is the smallest instrument on the market today. This synthesizer is a stand-alone synthesis with a small footprint, and allows the use of one mL up to 125 mL reaction vessels; the Discover™ System controls reaction temperatures, pressures, and stirring speeds.

"R" stands for alkyl radical, such as, but not limited to methyl, ethyl, propyl and the like.

"Standard mode" is a setting on CEM microwave reactors by means of which the power of microwave radiation that is delivered to the reaction cavity and is modulated in order to keep the specified temperature or pressure.

Compounds are numbered herein and are identified in the listing below:

Compound number: Chemical name and/or function 1 4-(phenylthio)benzaldehyde, a bis-phenyl sulfide
2 (4-(bromomethyl)phenyl)(phenyl)sulfide, a benzyl bromide
3 an alkylated fluorene
4 9,9-didecyl-2,7-diformylfluorene, an alkylated diformylfluorene
5 (4,4'-(1E,1'E)-2,2'-(9,9-didecyl-9H-fluorene-2,7-diyl)bis(ethene-2,1-diyl)bis(4,1-phenylene))bis(phenylsulfane), precursor compound 5
6 diphenyliodonium hexafluoro phosphate (V), a reagent.
7 (4,4'-(1E,1'E)-2,2'-(9,9-didecyl-9H-fluorene-2,7-diyl)bis(ethene-2,1-diyl)bis(4,1-phenylene))bis(diphenylsulfonium) hexafluorophosphate(V), a sulfonium salt and photoacid generator, PAG 7.
8 phenyl(4-vinylphenyl)sulfane
9 9,9-didecyl-2-iodo-7-nitro-9H-fluorene, a nitro-containing fluorene compound.
10 (E)-(4-(2-(9,9-didecyl-7-nitro-9H-fluoren-2-yl)vinyl)phenyl)(phenyl)sulfane, a stilbenyl sulfide precursor compound 10.
11 (E)-(4-(2-(9,9-didecyl-7-nitro-9H-fluoren-2-yl)vinyl)phenyl)diphenylsulfonium hexaflourophosphate (V), a sulfonium salt and photoacid generator, PAG 11.
12 9,9-didecyl-7-nitro-9H-fluoren-2-yl)(phenyl)sulfane
13 (9,9-didecyl-7-nitro-9H-fluoren-2-yl)diphenylsulfonium hexafluorophosphate(V), PAG 13
14 1-(5-bromothiophen-2-yl)ethanone, a brominated acetylthiophene derivative
15 (E)-1-(5-bromothiophen-2-yl)-3-(4-(phenylthio)phenyl)prop-2-en-1-one, precursor 15
16 (E)-(4-(3-(5-bromothiophen-2-yl)-3-oxoprop-1-enyl)phenyl)diphenylsulfonium hexafluorophosphate(V), PAG 16
17 An alkylphenyl sulfide
18 A diphenylmethylsulfonium salt
19 A diaryl sulfide
20 A triarylsulfonium salt
21 A diaryl sulfide
22 (4-formylphenyl)diphenylsulfoniumhexafluorophosphate(V), PAG 22

The present invention provides efficient methods for preparing sulfonium photoacid generators (PAGs) by microwave-assisted reaction of diphenylsufides in the presence of diphenyliodonium salts. Several of the PAGs are novel and have potential for use as 2PA photoinitiators in negative resists for 3D microfabrication or in optical data storage. Furthermore, the efficiency of forming these sulfonium salts by the microwave-assisted process was evaluated relative to the conventional thermal reaction of diphenylsulfides in the presence diphenyliodonium salts. Finally, photoacid quantum yields were determined for several of the novel PAGs.

The new PAGs were designed to exhibit high two-photon absorbing (2PA) cross sections. Because of its high thermal and photochemical stability, fluorene was chosen as the core structure of the PAGs, as discussed by Belfield, K. et al. in *Photochem. Photobiol. Sci.* 2004, 3, 138-141. Quite advantageously, fluorene lends itself to ready substitution in its 2-, 7-, and 9-positions. Stilbene or thiophene motifs were introduced in 2- and 7-positions, in order to extend the π-conjugation. Ultimately, two acceptor groups (triarylsulfonium and nitro) are introduced.

Example 1

Microwave-Assisted Synthesis of Sulfonium Salts

As an example of the general procedure for the microwave-assisted preparation of sulfonium salts. The preparation of (4,4'-(1E,1'E)-2,2'-(9,9-didecyl-9H-fluorene-2,7-diyl)bis (ethene-2,1-diyl)bis(4,1-phenylene))bis(diphenylsulfonium) hexafluorophosphate (V), PAG 7.
Materials.

Compounds 1 (formyl phenyl phenyl sulfide) and 4 (9,9-didecyl-2,7-diformylfluorene) in FIG. 1 were synthesized according to methods reported in Sivasubramaniam, S. et al. *Indian Journal of Chemistry Section B—Organic Chemistry Including Medicinal Chemistry* 1991, 30, 1148-1149 and Belfield, K. D. et al., in Polymers for Advanced Technologies 2005, 16, 150-155, respectively. Thioanisole and phenyl sulfide were used as provided by suppliers. All glassware was flame dried and cooled in a dessicator over calcium chloride. All reactions were carried out under nitrogen atmosphere.

All sulfonium salt synthesis and purification were carried out under yellow light, red light, or in the dark. The sulfonium salt preparation, when carried out by conventional heating methods, was done according literature procedures using chlorobenzene as a solvent.

In a 2 mL glass reaction vessel, purchased from CEM Corporation, microwave reactor manufacturer (heavy walled vessels with corresponding septum designed to withstand up to 3000 psi inside the reaction chamber), 0.21 g (0.24 mmol) of 5, 0.21 g (0.48 mmol) of diphenyliodonium hexafluoro phosphate (V), 6, and 0.006 g (5% molar) copper(II) benzoate were mixed in the dark in 2 mL of chlorobenzene while being purged with $N_2$. The microwave was set to closed vessel standard mode; maximum pressure 40 psi; maximum temperature 125° C., maximum power 100 W, high speed stirring. The run time (time at which the reaction reaches max temperature or pressure) was set for 30 s and the hold time for 1 min. The reaction was monitored by thin layer chromotography (TLC) until most of the starting material had disappeared. Rarely did sulfides convert entirely. In the cases in which the reaction time was extended to try to achieve full conversion, side products seriously complicated the purification hindering the overall yield of the sulfonium salt.

Upon completion, 12 min hold time, the solvent was vacuum distilled affording a dark yellow crude. $^1$H NMR revealed the presence of what appeared to mono-(45%) and bis-sulfonium (55%). The derivatives which were separated by column chromatography using hexane:ethyl acetate 6:4 as eluent, the faster eluting fraction (likely the mono-sulfonium) quickly decomposed and wasn't characterized. The second fraction was a dark yellow solid (0.239 g, 77%): Mp 63.5-65.8° C.; $^1$H NMR (500 MHz, acetone-$d_6$) 8.08 (d, 10 Hz, 4H), 7.93 (m, 28H), 7.70 (m, 4H), 7.53 (d, 20 Hz, 2H), 2.15 (m, 4H), 1.14 (m, 28H), 0.78 (t, 5 Hz, 6H), 0.65 (m, 4H). $^{13}$C NMR (125 MHz, acetone-$d_6$) 151.8 (C), 144.4 (C), 141.7 (C), 136.0 (C), 134.7 (CH), 134.5 (C), 131.9 (CH), 131.6 (CH), 131.2 (CH), 129.0 (CH), 126.9 (C), 125.5 (C), 125.3 (CH), 121.8 (C), 120.5 (C), 120.4 (C), 55.1 (C), 40.0 (C), 31.7 (C), 23.6 (C), 22.3 (C), 13.5 (C). Elemental Analysis Calcd. for ($C_{73}H_{80}F_{12}P_2S_2$): C, 66.85; H, 6.15; S, 4.89. Found: C, 66.94; H, 6.28; S, 4.69.

In FIG. 1, the synthesis of a photoacid generator with the chemical structure 7 (hereinafter PAG 7) shows the reaction conditions for both conventional methods (Δ) and microwave heating (MW). In order to enhance the photoacid quantum yield per molecule, the first approach was to incorporate two sulfonium salt motifs 1 and 2 onto the fluorenyl scaffold 3 and 4, in a process that forms a precursor compound 5 that is reacted with diphenyl iodium 6 to form a photoacid generator having a chemical structure 7. Diphenyl iodonium 6 is a reagent. This reagent is known to undergo thermolysis between 115-120° C. in presence of a copper catalyst. Upon thermolysis Compound 6 delivers a phenyl group to the sulphide, thus forming the sulfonium salt and simultaneously delivering the counterion to a positively charged sulfonium scaffold.

In FIG. 1, the precursor bis-sulfide 5 was prepared by a convergent synthesis of benzyl bromide 2 and 9,9-didecyl-2,7-diformylfluorene 4. The phosphonate was obtained from 4-(phenylthio)benzaldehyde which was first reduced with $NaBH_4$ (10% in silica) aided by conventional, multimode microwave radiation, as disclosed by Varma, R. S. et al. in *Tetrahedron Letters*, 1997 38, 4337-4338. Since hydrogen is extruded during the reaction, when carried out in scales larger than 0.500 g safety concerns dictated running the reaction at room temperature for 24 h.

The resulting alcohol was refluxed in HBr (33% in AcOH) to obtain the benzylic bromide intermediate, subsequently used to obtain the bisphosphonate. The second branch of the synthesis started from fluorene, alkylation of the 9-position with bromodecane imparted the desired solubility to alkylated fluorene molecule 3, as reported by Belfield, K. et al. in *J. Org. Chem.* 2000, 65, 4475-4481.

Bromination with NBS (N-bromosuccinimide) of the 2- and 7-positions of the alkylated fluorene 3 was followed by introduction of the formyl group. A bisformyl fluorene, 9,9-didecyl-2,7-diformylfluorene 4 and the bisphosphonate were coupled via a Wadsworth-Horner-Emmons reaction, yielding exclusively the trans-isomer 5. Bis-sulfide 5 was the precursor for bis-sulfonium salt 7 under both conventional and microwave-assisted procedures.

The molecule, PAG 7, exhibited high fluorescence quantum yield (0.80), limiting the photoacid quantum yield to (0.03) when excited at 400 nm. The direct photolysis of triarylsulfonium salts has been reported to occur primarily from the first excited singlet state. However, sensitization studies have shown that triplet triarylsulfonium salts are also labile, as reported by Dektar, J. L. et al. in *J. Am. Chem. Soc.* 1990, 112, 6004-6015. Consequently, a decision was made to incorporate a nitro group in the structures to induce intersystem crossing.

Figure 2:
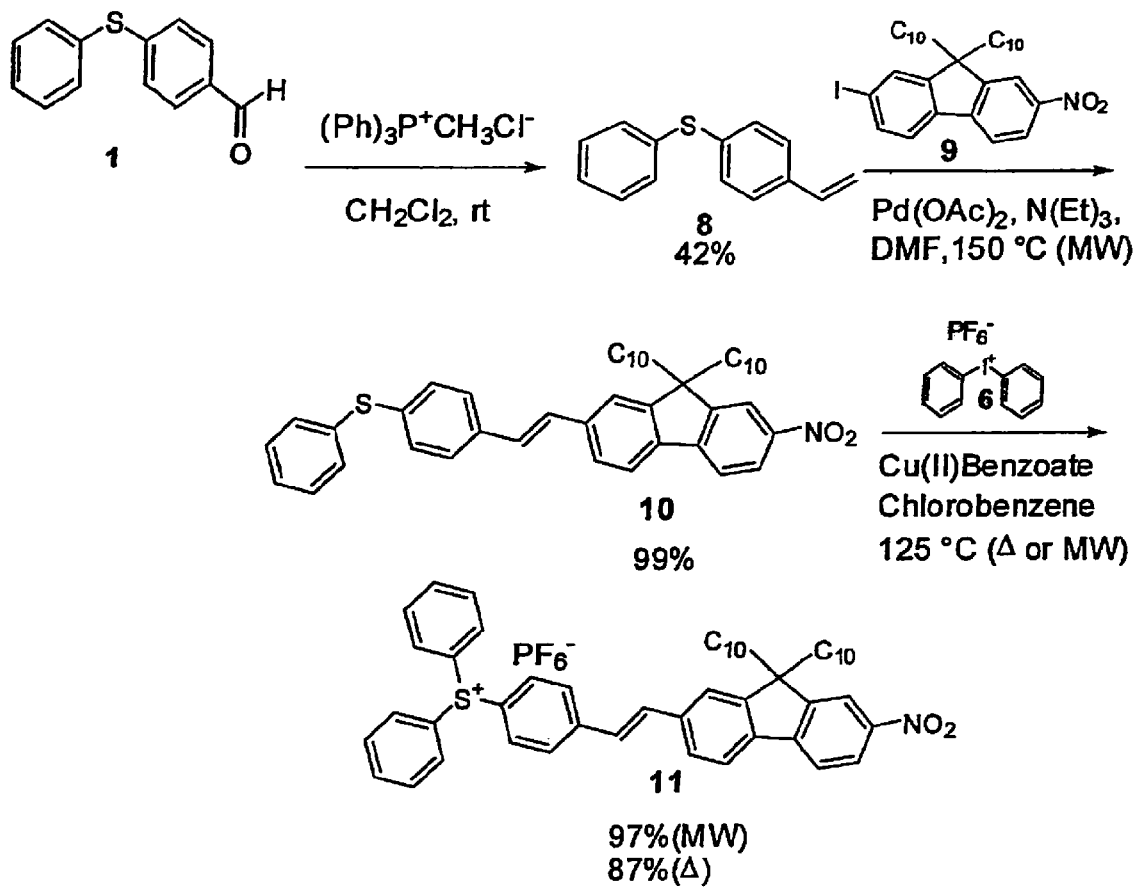
FIG. 2 shows a synthesis scheme for a photoacid generator PAG 11, wherein conventional reactions are carried out at 125° C. and microwave-assisted synthesis is carried out with 100 watts energy input, closed vessel, standard mode; 40 psi.
Figure 3:
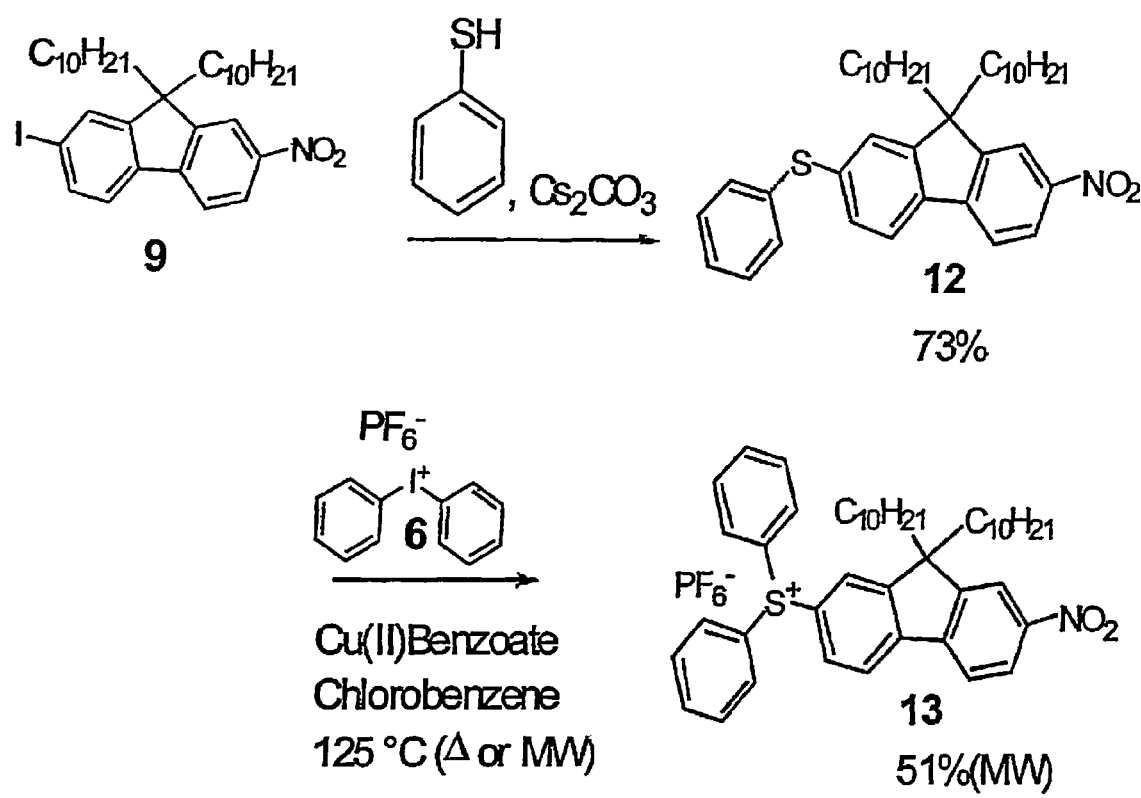
FIG. 3 shows a synthesis scheme for a photoacid generator PAG 13, wherein a first microwave assisted reaction occurs under reaction conditions including 190° C.; 100 watts microwave energy, closed vessel, standard mode; 40 psi forming precursor compound 12 and a second microwave-assisted reaction occurs in the presence of diphenyl iodonium under reaction conditions including, 125° C., 150 watts microwave energy, closed vessel, standard mode; 100 psi forming PAG 13, at 51% yield. Conventional synthesis reactions are carried out at 125° C.

FIGS. 2 and 3 show the synthesis of sulfonium salts 11 and 13, respectively, using the versatile 2-iodo-7-nitro-9,9-didecylfluorene precursor 9. The versatile 2-iodo-7-nitro-9,9-didecylfluorene precursor 9 was prepared as reported by Belfield et al. in *J. Org. Chem.* 2000, 65, supra. Interestingly, (E)-(4-(2-(9,9-didecyl-7-nitro-9H-fluoren-2-yl)vinyl)phenyl)(phenyl)sulfane 10 was obtained quantitatively via a microwave-assisted palladium acetate-catalyzed Heck reaction, coupling vinyl sulfide 8 and precursor 9. The yields for both conventional and microwave-assisted methods were the highest for PAG 11 of the entire series. Fluorenylphenylsulfide 12 was prepared from Cu-catalyzed S-arylation of 9 and thiophenol.

In FIG. 2, the synthesis scheme for PAG 11 is carried out by conventional means at a reaction temperature of 125° C. The microwave-assisted synthesis is carried out at 100 watts, closed vessel; 40 psi; 125° C. In all of the microwave assisted reactions reported here the maximum established temperature is reached before the maximum established pressure, so the first is the parameter that is used to control the dose of microwave radiation that was delivered to the reaction cavity. Percentages indicate percent yield. The side products of the reactions were not characterized and the percent conversions were not determined because the reaction yields are high enough for these factors to be irrelevant. A step by step detailed description of the reaction conditions of all new compounds can be found in the supplementary information section. Among the conditions stated are reaction temperatures, times, and pressures both for conventional and microwave assisted reactions. In this section you will also find the characterization of each new compound by $^1$H NMR, $^{13}$C NMR and elemental analysis.

In FIG. 3, the synthesis scheme for PAG 13 is carried out as follows:

As a result of incorporating the nitro group in the structures as shown in FIGS. 2 and 3, the fluorescence quantum yield of precursors 10 (in FIG. 2) and 12 (in FIG. 3), and sulfonium salts 11 (in FIG. 2) and 13 (in FIG. 3), were significantly decreased (Table 1), thereby reducing the radiative decay pathway. Nitro-containing sulfonium salt 11 exhibited an increased photoacid quantum yield (Table 1). The photoacid quantum yields were determined by a steady state method in which solutions of the PAGs in acetonitrile were selectively irradiated at the desired wavelength with an excitation source and monochromater of a spectrofluorimeter. Rhodamine B was used as a sensor for photoacid generation, as reported by Pohlers, G. et al, in *Chem. Mater.* 1997, 9, 1353-1361.

Special care was taken to record the photodecomposition conversion no greater than 5% in order keep secondary photoproduct generation to a minimum. Previously, we determined a number of photochemical quantum yields under one- and two-photon excitation, and found no significant difference relative to excitation mode. Hence, the values of quantum yields in Table 1 are good estimates under 2PA, as reported by Corredor, C. C., et al. in *J. Photochem. Photobiol., A*, 2006, 184, 177-183.

TABLE 1

Fluorescence quantum yields and photoacid quantum yields of sulphide precursors and PAGs.

| Compound | $\Phi_F$ | $\Phi_{H+}$ |
|---|---|---|
| 5 | 1.0 | — |
| 7 | 0.8 | 0.03[a] |
| 10 | 0.0 | — |
| 11 | 0.0 | 0.16[a]; 0.03[b] |
| 12 | 0.0 | — |
| 13 | 0.0 | 0.01[b]; 0.04[d] |
| 20 | — | 0.53[c] |

Figure 4:
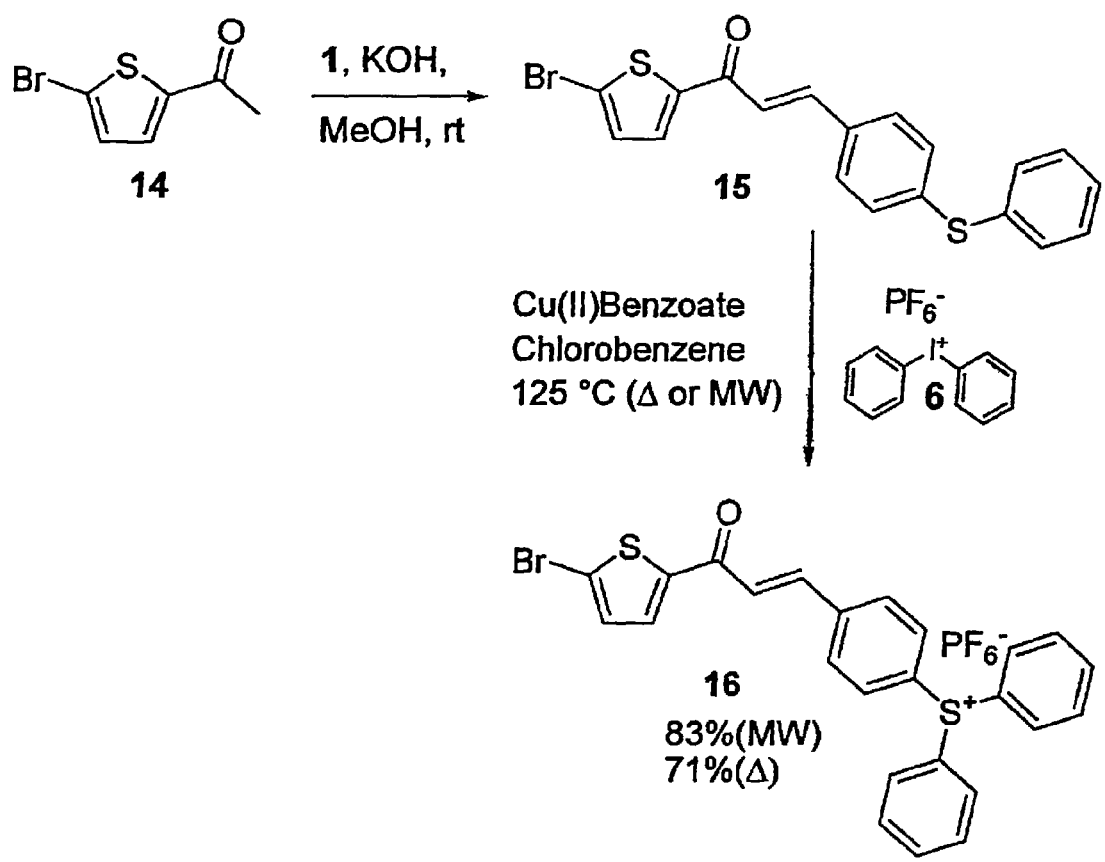
FIG. 4 shows a synthesis scheme for a photoacid generator PAG 16, wherein reaction conditions include reacting a precursor compound 15 in the presence of Cu(II) benzoate and chlorobenzene at 125° C. for both conventional and microwave-assisted synthesis, with microwave energy at 100 watts (W), closed vessel, standard mode; 40 psi. Microwave-assisted synthesis yield is 83% in six minutes; conventional synthesis yield is 71% after 24 hours reaction time.

[a]400 nm irradiation;
[b]350 nm irradiation.
[c]Dektar, J. L. *J. Org. Chem.*, 1990, 55, 639-647;
[d]270 nm irradiation A diphenyl sulfide, (E)-1-(5-bromothiophen-2-yl)-3-(4-(phenylthio)phenyl) prop-2-en-1-one 15 was prepared to evaluate how the thiophene and chalcone functionalities would withstand the rapid heating conditions of the microwave-assisted (MW) method, further demonstrating the versatility of the MW-method. Precursor 15 resulted from a straightforward Claisen condensation of 1-(5-bromothiophen-2-yl)ethanone, a brominated acetylthiophene derivative 14 and formyl phenyl phenyl sulfide 1 as shown in FIG. 4. Both functionalities were intact after the microwave assisted reaction was carried out.

In FIG. 4, the synthesis scheme for PAG 16 is carried out as follows: A brominated acetylthiophene derivative, 1-(5-bromothiophen-2-yl)ethanone (14) is reacted with 4-(phenylthio)benzaldehyde (1) in the presence of methanol and potassium hydroxide at room temperature to form a precursor compound, (E)-1-(5-bromothiophen-2-yl)-3-(4-(phenylthio)phenyl)prop-2-en-1-one (15). The precursor compound (15) is exposed to microwave heating at 125° C. in the presence of diphenyliodonium hexafluoro phosphate (V) (6) to form a photoacid generator, (E)-(4-(3-(5-bromothiophen-2-yl)-3-oxoprop-1-enyl)phenyl)diphenylsulfonium hexafluorophosphate(V), identified herein as PAG 16. The reactions are carried out by conventional heating (Δ) and microwave heating (MW) and the Quantum yield per molecule of PAG 16 is 71% for conventional heating (Δ) and 83% for microwave heating (MW).

Figure 5:
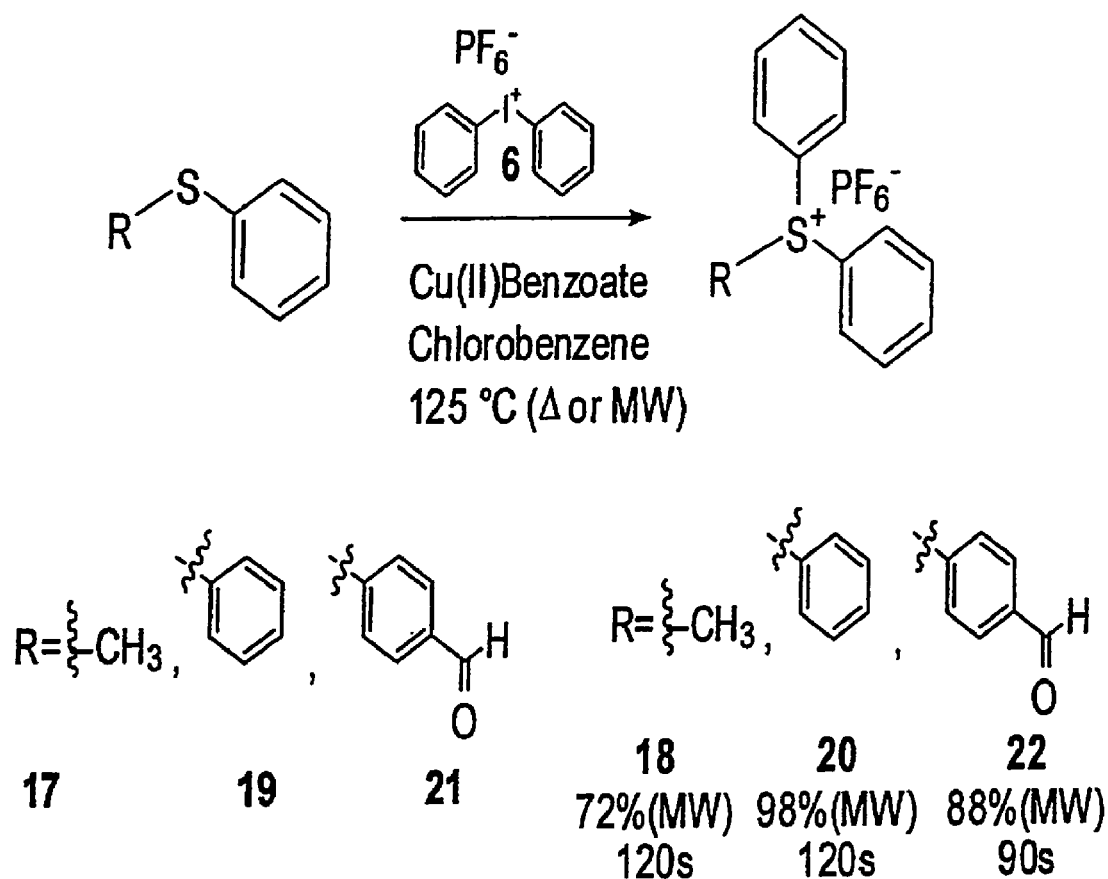
FIG. 5 shows a synthesis scheme for several photoacid generators PAG 18, PAG 20, PAG 22 wherein the reaction conditions include 125° C. for conventional synthesis and microwave-assisted synthesis conditions include 100 watts (W), closed vessel, standard mode; 40 psi; and 125° C.
Figure 6:
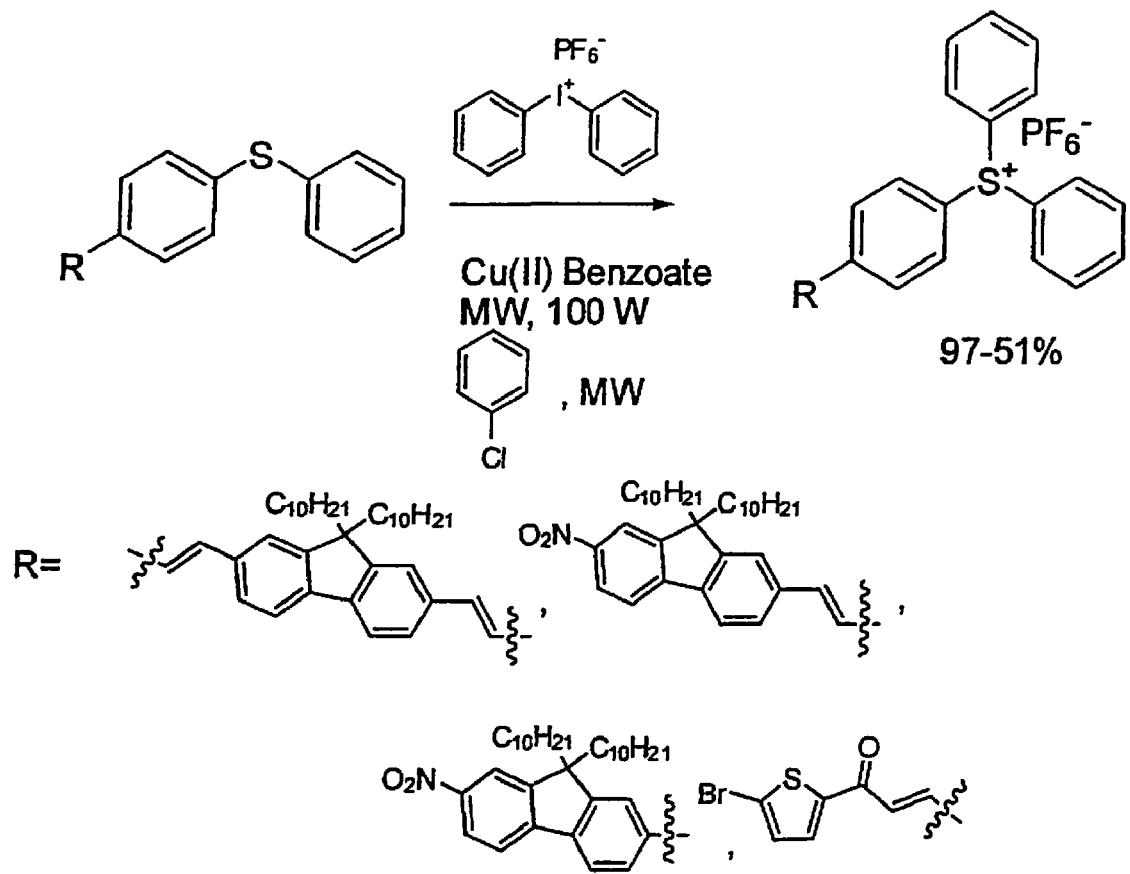
FIG. 6 shows a synthesis scheme for sulfonium photoacid generators having a fluorenyl scaffold.

Furthermore, we sought to compare the effectiveness of this method when performed on less conjugated sulfides that may be more relevant in UV or deep UV lithographic applications in FIG. 5.

In FIG. 5, a commercially available phenyl sulfide is reacted with diphenyl iodonium hexafluorophosphate (V) to prepare the precursor compound for sulfonium salt, (4-formylphenyl)diphenylsulfonium hexafluorophosphate (V), PAG 22.

The preparation of sulfonium salt 22 was carried out according to the general procedure reported above from the commercially available sulfide 21. After purification, a colorless solid was obtained (0.378 g, 88%). $^1$H NMR (500 MHz, acetone-d$_6$) 10.24 (s, 1H), 834 (d, 9 Hz, 2H), 8.15 (d, 9 Hz, 2H), 8.08 (m, 6H), 7.91 (t, 9 Hz, 4H) $^{13}$C NMR (125 MHz, acetone-d$_6$) 191.2 (CHO), 140.3 (C), 135.0 (C), 131.9 (CH), 131.7 (CH), 131.6 (CH), 131.5 (CH), 130.8 (C), 124.4 (CH), C$_{19}$H$_{15}$F$_6$OPS: C, 52.30; H, 3.46; S, 7.35. Found: C, 52.47; H, 3.43; S, 7.25.

The yields of 18 and 20 were comparable to those reported in the literature. As in the previous precursors, microwave heating significantly reduced reactions times for the formation of these sulfonium salts when compared to conventional heating times performed by using reagent 21, or reported in the literature, product 20 and product 22 in Table 2 below.

TABLE 2

Microwave-assisted vs Conventional Heating Reaction Times for Sulfonium Salt PAG Formation.

| Reagent | Product | MW Time (Yield) | Δ Time (Yield) |
|---|---|---|---|
| 5 | 7 | 6 min (75%) | 29 h (42%) |
| 10 | 11 | 8 min (97%) | 8 h (87%) |
| 12 | 13 | 10 min (51%) | 70 h (10%) |
| 15 | 16 | 14 min (83%) | 24 h (71%) |
| 17 | 18 | 120 s (72%) | 3 h (100%)[a] |
| 19 | 20 | 120 s (98%) | 3 h (97%)[b] |
| 21 | 22 | 90 s (88%) | 3 h (83%) |

[a]Beak, P. et al. *J. Am. Chem. Soc.*, 1982, 104, 4450-4457.
[b]Crivello, J.V. *J. Org. Chem.* 1978, 43, 3055-3058.

The reactions that were carried out under conventional conditions, in Table 2, were performed in an oil bath heated to 120° C. at atmospheric pressure; whereas, the microwave-assisted reactions were run at the same temperature in closed vessel mode, reaching pressures no higher that 30 psi.

In every case, the reactions that were heated conventionally took significantly longer than the analogous microwave reactions, and microwave-assisted yields were higher.

In conclusion, the present invention provides a new, more favorable methodology for the formation of sulfonium salts via microwave-assisted decomposition of diphenyliodonium salts in the presence of diphenylsulfides. Microwave-assisted reaction times were 90 to 420 times faster, resulting in generally higher yields. In addition, the introduction of groups that favor intersystem crossing is a viable means for increasing the photoacid quantum yield of novel triarylsulfonium salt photoacid generators (PAGs).

Commercial manufacturers of sulfonium PAGs for use in the photolithography and coatings industries can prepare PAGs faster, easier, and more efficiently, while realizing production energy cost savings. By shortening reaction time from hours, approximately 20 hours at elevated temperatures in a range of 125° C., to minutes, approximately 6-10 minutes, using the process of the present invention, greater efficiencies and lower energy consumption is achieved. Uniformly higher yields than conventional thermal methods are provided by the present invention While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method for formation of sulfonium salts comprising the steps of:
   providing a diaryl iodonium salt in the presence of a diaryl sulfide; and
   exposing the diaryl iodonium salt in the presence of the diaryl sulfide to microwave radiation that is delivered to a closed reaction cavity and is modulated for a maximum pressure of approximately 40 psi, a maximum temperature of approximately 125° C. and a maximum power of 100 watts with stirring for assisted formation of a triaryl sulfonium salt photoacid generator wherein the reaction time for the formation of the sulfonium salt photoacid generator is in a range from approximately 30 seconds to approximately 10 minutes.

2. The method of claim 1, wherein the diaryl iodonium salt is selected from at least one of a diphenyl iodonium salt.

3. The method of claim 1, wherein the diaryl sulfide is selected from at least one of a diphenyl sulfide.

4. The method of claim 1, wherein the diaryl iodonium salt further includes a fluorene compound.

5. The method of claim 4, wherein the fluorene compound is substituted with at least one of a stilbene motif, a thiophene motif and a nitro group at the 2- and 7-positions.

6. The method of claim 4, wherein the fluorene compound is substituted with a nitro group at the 7-position.

7. The method of claim 1, wherein the reaction time for the formation of the sulfonium salt photoacid generator is in a range from approximately 3 minutes to approximately 10 minutes.

8. The method of claim 7, wherein the reaction time for the formation of the sulfonium salt photoacid generator is approximately 6 minutes.

9. A method for increasing the efficiency of photoacid generation by preparing a nitro-containing sulfonium salt and inducing intersystem crossing by a process consisting essentially of:
   selecting a glass reaction vessel suitable for use in a microwave reactor;
   mixing a fluorene compound that incorporates a nitro group with a diarylsulfide in the glass reaction vessel to form mixture I;
   purging the mixture I with nitrogen gas while stirring;
   placing the glass reaction vessel containing the nitrogen purged mixture I in the microwave reactor;
   setting the microwave reactor containing the mixture I of nitro-group fluorene compound and diarylsulfide to closed vessel, standard mode; maximum pressure 250 psi, maximum temperature 150 C, maximum power 60 watts and high speed stirring;
   running the microwave reactor for thirty seconds and holding for 30 minutes;
   removing a nitro-containing, triarylsulfonium salt that exhibits increased photoacid quantum yield in a range of from approximately 0.01 to approximately 0.4 times greater than yields from conventional synthesis.

10. The method of claim 9, wherein the fluorene compound that incorporates a nitro group is 9,9-didecyl-2-iodo-7-nitro-9H-fluorene.

11. The method of claim 9, wherein the diarylsulfide is vinyl sulfide.

12. The method of claim 4, wherein the fluorene compound included in the diaryl iodonium salt forms the core structure of the triaryl sulfonium salt photoacid generator formed by the microwave radiation assisted reaction of the diaryl iodonium salt including a fluorene compound and the diaryl sulfide.

13. The method of claim 1, wherein the sulfonium salt photoacid generator formed is: PAG 7, which is the compound having the chemical name (4,4'-(1E,1'E)-2,2'-(9,9-didecyl-9H-fluorene-2,7-diyl)bis(ethene-2,1-diyl)bis(4,1-phenylene))bis(diphenylsulfonium) hexafluorophosphate (V).

14. The method of claim 1, wherein the sulfonium salt photoacid generator formed is: PAG 11, which is the compound having the chemical name (E)-(4-(2-(9,9-didecyl-7-nitro-9H-fluoren-2-yl)vinyl)phenyl)diphenylsulfonium hexafluorophosphate (V).

15. The method of claim 1, wherein the sulfonium salt photoacid generator formed is: PAG 13, which is the compound having the chemical name (9,9-didecyl-7-nitro-9H-fluoren-2-yl)diphenylsulfonium hexafluorophosphate(V).

16. The method of claim 1, wherein the sulfonium salt photoacid generator formed is: PAG 16, which is the compound having the chemical name (E)-(4-(3-(5-bromothiophen-2-yl)-3-oxoprop-1-enyl)phenyl)diphenylsulfonium hexafluorophosphate(V).

17. The method of claim 1, wherein the sulfonium salt photoacid generator formed is: PAG 22, which is the compound having the chemical name (4-formylphenyl)diphenylsulfonium hexafluorophosphate(V).

* * * * *